United States Patent [19]
Müllner et al.

[11] Patent Number: 5,834,265
[45] Date of Patent: *Nov. 10, 1998

[54] MULTIFUNCTIONAL RNA HAVING SELF-PROCESSING ACTIVITY, THE PREPARATION THEREOF AND THE USE THEREOF

[75] Inventors: Hubert Müllner, Kelkheim; Eugen Uhlmann, Glashütten; Peter Eckes; Rudolf Schneider, both of Kelkheim; Bernadus Uijtewaal, Heythuysen, all of Germany

[73] Assignee: Hoechst Aktiengesellschaft, Frankfurt am Main, Germany

[*] Notice: The term of this patent shall not extend beyond the expiration date of Pat. No. 5,707,840.

[21] Appl. No.: 459,324

[22] Filed: Jun. 2, 1995

Related U.S. Application Data

[62] Division of Ser. No. 313,608, Sep. 29, 1994, Pat. No. 5,707,840, which is a continuation of Ser. No. 73,295, Jun. 7, 1993, abandoned, which is a continuation of Ser. No. 592,655, Oct. 4, 1990, abandoned.

[30] Foreign Application Priority Data

Oct. 6, 1989 [DE] Germany .......................... 39 33 384.1

[51] Int. Cl.$^6$ .............................. C12N 15/63; C12N 5/04; C12N 15/82; A61K 48/00
[52] U.S. Cl. .................................. 435/172.1; 435/320.1; 435/419; 514/44; 536/24.5
[58] Field of Search ................. 435/419, 172.1, 435/410, 320.1; 514/44; 536/24.5; 800/205, 250

[56] References Cited

U.S. PATENT DOCUMENTS 4,987,071  1/1991  Cech et al. ........................... 435/91.31

FOREIGN PATENT DOCUMENTS 0 321 201 A2  6/1989  European Pat. Off. .
WO 89/05852  6/1989  WIPO .

OTHER PUBLICATIONS

Doudna and Szostak. RNA–catalyzed synthesis of complementary–strand RNA. Nature. vol. 339:519–522, Jun. 15, 1989.

Haseloff and Gerlach. Simple RNA enzymes with new and highly specific endoribonuclease activities. Nature. vol. 334:585–591, Aug. 18, 1988.

Walbot and Bruening. Plant development and ribozymes for pathogens. Nature. vol. 334:196–197, Jul. 21, 1988.

Rezaian et. al.. Anti–sense RNs of cucumber mosaic virus in transgenic plant assessed for control of the virus. Plant Mol. Biol. 11:463–471, Nov. 7, 1988.

Rezaian et al., "Anti–sense RNAs of Cucumber Mosaic Virus in Transgenic Plants Assessed for Control of the Virus," Plant Molecular Biology 11:463–71 (1988).

Cuozzo et al., "Viral Protection in Transgenic Tobacco Plants Expressing the Cucumber Mosaic Virus Coat Protein or Its Antisense RNA," Biotechnology 6(5):549–57 (1988).

Forster et al., "Self–cleaving Viroid and Newt RNAs May Only Be Active As Dimers," Nature 334:265–67 (1988).

Walbot et al., "Plant Development and Ribozymes for Pathogens," Nature 334:196–97 (1988).

Knight, "Biocatalysts By Design," Bio–Technology 6(7):826–27 (1988).

Chuat et al., "Can Ribozymes Be Used to Regulate Procaryote Gene Expression?," Biochemical and Biophysical Research Communications 162(3):1025–29 (1989).

Cotten, "The In Vivo Application of Ribozymes," Tibtech 8:174–78 (1990).

Rossi et al., "RNA Enzymes (Ribozymes) As Antiviral Therapeutic Agents," Tibtech 8:179–83 (1990).

Chang et al., "Ribozyme–Mediated Site–Specific Cleavage of the HIV–1 Genome," Clinical Biotechnology 2(1):23–31 (1990).

Evans et al., "The Effects of Ribozymes on Gene Expression in Plants," Biochemical Society Transactions 20:344S (1992).

Primary Examiner—Nancy Degen
Assistant Examiner—William Sandals
Attorney, Agent, or Firm—Finnegan, Henderson, Farabow, Garrett & Dunner, L.L.P.

[57] ABSTRACT

A multifunctional RNA having self-processing activity, the preparation thereof and the use thereof Host cells can be transformed so that they express ribozyme RNA and antisense RNA which are connected with each other via a spacer. The RNA molecules can, for example, be complementary to a certain viral RNA. Plants which have been transformed with genes coding for RNA of this type show a significantly improved resistance to viruses.

8 Claims, 6 Drawing Sheets

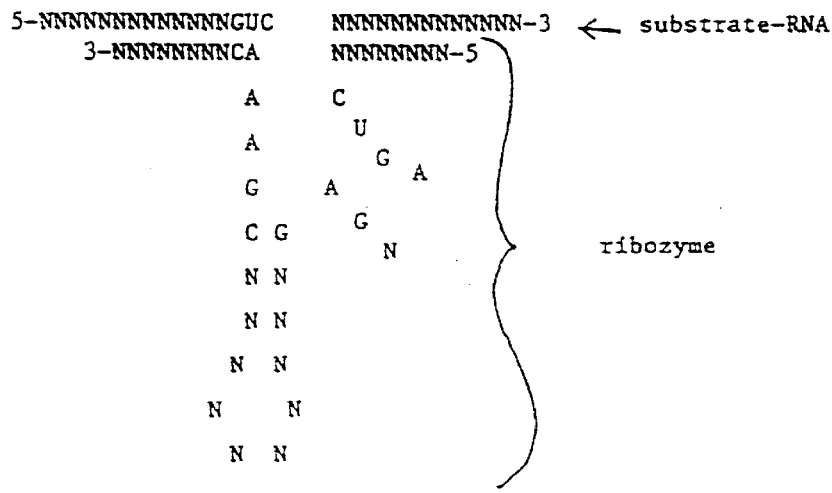

wherein

N    in the substrate-RNA are nucleotides of the substrate RNA, A, C, G or U

N    in the ribozyme-RNA, starting at the 5' end, are as follows:

at positions 1-8 and 33-40, are complementary nucleotides to N in the substrate-RNA at positions 13, 17, 18, 25 are variable nucleotides, A, C, G, or U, in the ribozyme at positions 19-24 are variable nucleotides, A, C, G or U, in the loop of the ribozyme, wherein the number of the nucleotides can be 0-550.

FIGURE 1

Figure: 10 μg total DNA, digested with EcoRI, hybridized with entire fragment

1) λ PST
2) Control
3) A-H1
4) A-H3
5) A-H4
6) A-H5
7) A-H6
8) A-H7
9) A-H9
10) A-H10
11) A-H12
12) A-H15
13) A-H22

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 479 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
CCGGGAGGTA  GCTCCTGATG  AGTCCGTGAG  GACGAAACAA  CCTTGTCGTC  GACAAAATGG    60

TCAGTATGCC  CCTCGAGTGG  TCTCCTTATG  GAGAACCTGT  GGAAAACCAC  AGGCGGTACC   120

CGCACTCTTG  GTAATATCAG  TGTATTACCG  TGCACGAGCT  TCTCACGAAG  CCCTTCCGAA   180

GAAATCTAGG  AGATGATTTC  AAGGGTAGCT  CGACAACCTG  GATCCAAAAT  GGTCAGTATG   240

CCCCCCATGG  CAACAGATTG  GCGAATGAGA  AAGTGGGTGG  AGGACTTATC  ATAGTAACAG   300

AAGAGAGACT  AGAACTGCAG  AAAATGGTCA  GTATGCCCCA  GATCTACCGG  AGGTTCTACT   360

AGCATTGGGA  GAGCTCGATT  TGTCCATAGG  CACACTGAGA  CGCAAAAAGC  TTAAGGTTGT   420

CGAGCTACCG  GGGCCCAGGG  CATACTCTGA  TGAGTCCGTG  AGGACGAAAC  CATTTTGGG    479
```

( 2 ) INFORMATION FOR SEQ ID NO:2:

( i ) SEQUENCE CHARACTERISTICS:
        ( A ) LENGTH: 477 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
CCCAAAATGG  TTTCGTCCTC  ACGGACTCAT  CAGAGTATGC  CCTGGGCCCC  GGTAGCTCGA    60

CAACCTTAAG  CTTTTTGCGT  CTCAGTGTGC  CTATGGACAA  ACTGAGCTCT  CCCAATGCTA   120

GTAGAACCTC  CGGTAGATCT  GGGGCATACT  GACCATTTTC  TGCAGTTCTA  GTCTCTCTTC   180

TGTTACTATG  ATAAGTCCTC  CACCCACTTT  CTCATTCGCC  AATCTGTTGC  CATGGGGGGC   240
```

```
ATACTGACCA  TTTTGGATCC  AGGTTGTCGA  GCTACCCTTG  AAATCATCTC  CTAGATTTCT       300

TCGGAAGGGC  TTCGTGAGAA  GCTCGTGCAC  GGTAATACAC  TGATATTACC  AAGAGTGCGG       360

GTACCGCCTG  TGGTTTTCCA  CAGGTTCTCC  ATAAGGAGAC  CACTCGAGGG  GCATACTGAC       420

CATTTTGTCG  ACGACCAGGT  TGTTTCGTCC  TCACGGACTC  ATCAGGAGCT  ACCTCCC          477
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:3:

```
NNNNNNNNNN  NNNGUCNNNN  NNNNNNNNNN                                           30
```

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:4:

```
NNNNNNNNCU  GANGAGNNNN  NNNNNNCGAA  ACNNNNNNNN                               40
```

MULTIFUNCTIONAL RNA HAVING SELF-PROCESSING ACTIVITY, THE PREPARATION THEREOF AND THE USE THEREOF

This is a division of application Ser. No. 08/313,608, filed Sept. 29,1994, now U.S. Pat. No. 5,707,840, Jan. 13, 1998 which is a continuation of application Ser. No. 08/073,295, filed Jun. 7,1993, abandoned, which is a continuation of originally filed application Ser. 07/592,655, filed Oct. 4, 1990, abandoned.

RNA molecules can, under suitable conditions, catalyze reactions on other RNA molecules without the participation of proteins or autocatalytically cleave fragments of their own molecules. Thus an intron having 413 nucleotides is autocatalytically removed from the 3' end of the 23S rRNA of Tetrahymena thermophila and is transformed into a circular form. This takes place by a number of phosphoester transfer reactions with the participation of guanosine cofactors (Cech, T. R., Nature 30, 578–583 (1983)). Depending on the RNA substrate or the selected reaction conditions, the intron can function as a specific ribonuclease, terminal transferase, phosphotransferase or acid phosphatase. In this connection, an RNA molecule can carry out several reactions without itself being changed and, in this respect, behaves like an enzyme. For RNA molecules having these properties, the term ribozyme has therefore been introduced.

It has also been possible to show similar reactions without the participation of proteins for several viroid RNAs and satellite RNAS. Thus self-processing seems to be an essential reaction for the replication of Avocado Sunblotch Viroid (ASBV) (Hutchins, C. J. et al. Nucleic Acids Res. 14, 3627–3640 (1986)), satellite RNA from Tobacco Ringspot Virus (sTobRV) (Prody, G. A. et al, Science 231, 1577–1580 (1986)) and satellite RNA from Luzerne Transient Streak Virus (sLTSV) (Forster A. C. et al., Cell 49, 211–220 (1987)). Circular forms which, as templates, lead to the synthesis of extra long RNAs, are probably formed during the replication of these RNAS. These transcripts are cut to the appropriate length genome by the autocatalytic endonucleolytic reactions.

The structures of the RNAs which are presumably adopted by these for the reduction have been described as hammer- heads (Forster A. C. et al., Cell 49, 211–220 (1987); Haseloff, J. et al., Nature 334, 585–591 (1988)).

The cleavage sites for these RNA enzymes are specific and must have certain structural preconditions in order to make processing possible.

It has now been found that host cells of any organism desired can be transformed using vectors which contain the DNA encoding ribozyme RNA coupled to antisense RNA so that the said DNA is expressed.

It is known that antisense RNA inhibits the gene expression in a number of procaryotic and eucaryotic cells, inter alia also in plant cells (Green, P. J. et al., Ann. Rev. Biochem. 55, 569 (1986)). Most of the mechanism of inhibition is still unclear. It is presumed that, in eucaryotic systems, double-stranded RNA is formed which hinders the transport of the MRNA to the cytoplasm.

Rezaian, M. et al. (Plant Mol. Biol. 11, 463 (1988)), for example, investigated the possibility of using antisense RNA as antiviral agent against Cucumber Mosaic Virus (CMV). However, the authors observed that the antiviral effectivity of the antisense RNA was unsatisfactory.

The coupling of the appropriate ribozyme RNA to the respective antisense RNA via a spacer effects now, for example, a more effective resistance to virus than could be shown by Rezaian however. Such a coupling of the RNA molecules thus in general effects an enhanced activity in transformed organisms which is directed against a substrate rather than only with respect to the activity as antiviral agent in plants.

The invention thus relates to
1. A gene coding for a ribozyme RNA sequence coupled to an antisense RNA sequence by a spacer.
2. Organisms which contain the gene specified under 1. or the corresponding RNA sequence.
3. The use of ribozyme RNA coupled to antisense RNA via a spacer as an agent in organisms which is directed against a substrate.

BRIEF DESCRIPTION OF THE DRAWINGS

FIG. 1 is a diagram of the ribozyme hybridized with substrate RNA. SEQ ID NO: 3 SEQ ID NO: 4 are shown.

Figure 2:
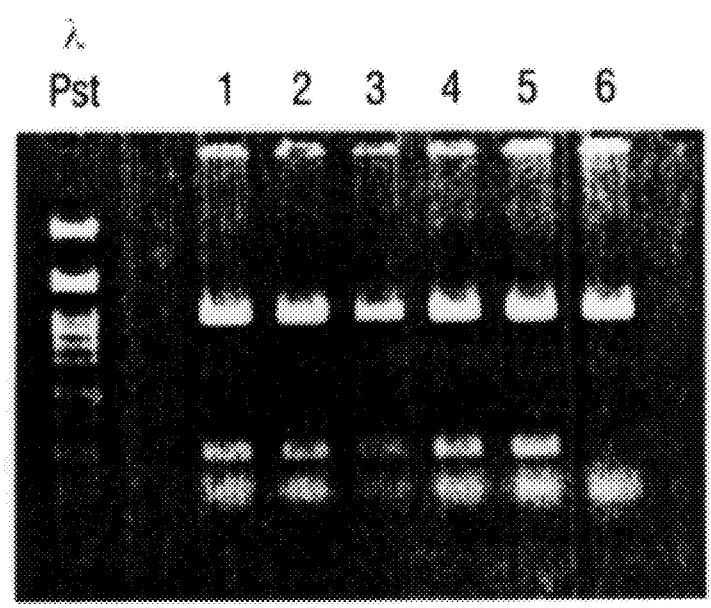
FIG. 2 is a photograph showing 6 colonies of a plasmid preparation from XL-1 Blue cells which were transformed with the vector pBluescript into the complete fragment has been incorporated.

The invention is described in detail in the following, in particular in its preferred embodiments. The invention is furthermore defined in the claims.

The multifunctional RNA according to the invention is essentially composed such that the ribozymes are at the 3' and the 5' end of the RNA molecule in each case. Antisense RNA units are inserted in between via so-called spacers, which RNA units can likewise be connected with each other via spacers if there are several units. Preferred embodiments of the multifunctional RNA molecule can, shown in a pattern, be as follows:

5'-Ribozyme RNA-spacer-(antisense RNA)$_n$-spacer-ribozyme RNA-3' in which n is a number from 1 to 10, preferably 1 to 5, in particular 1 to 3. A chain of 20 to 25 nucleotides which, as a whole or in a part comprising at least 8, preferably 10–20 nucleotides, is complementary to the sequence of the ribozyme is inserted as spacer. The ribozyme sequence of the RNA can in this way associate with the spacer and cut the latter immediately behind a recognition sequence. If the number n is greater than 1, a spacer of this kind having a ribozyme cleavage site is likewise inserted between the respective antisense RNA molecules. A GUC cleavage site is preferably incorporated as ribozyme cleavage site. The antisense RNA can be directed against substrates, such as for example RNA coding for selectable marker genes (resistances to antibiotics) or RNA coding for any cell function desired, such as dihydropholate reductase, thymidine kinase, the maturation enzymes polygalacturonase, pectinesterase etc., proteins responsible for differentiation and development or hormone receptors. In particular types of viruses damaging to plants can advantageously be combatted using the ribozyme-antisense system according to the invention. For this purpose, for example, the procedure as described in the following is carried out. The ribozyme antisense RNA which is directed against other substrates is also synthesized in an analogous procedure.

The DNA oligonucleotides coding for the multifunctional RNA can be prepared synthetically. The oligonucleotides for the antisense RNA can be synthesized on the basis of the viral DNA and RNA sequences. For this any plant-damaging virus can be used in principle. Preferred types of viruses are pathogenic RNA viruses, in particular Cucumber Mosaic Virus, Alfalfa Mosaic Virus, Brome Mosaic Virus, Tobacco Mosaic Virus, Potato Virus X or Y, Tomato Ringspot Virus, Tomato Aspermy Virus or Tobacco Rattle Virus.

At least 10 consecutive nucleotides, in particular 14 to 20 nucleotides, advantageously from the middle of the RNA sequence of the respective virus are preferred as template for the synthesis of the oligonucleotides encoding the ribozyme RNA. This RNA sequence can be both the genome of RNA viruses and an RNA sequence which has been derived from the DNA sequence of a DNA virus. It is particularly advantageous to use the 3 RNA sequences RNA1, RNA2 and RNA3 of the Cucumber Mosaic Virus or parts thereof as a basis, corresponding to the sequences from the publications by Rezaian M. et al., Eur. J. Biochem. 150, 331–339 (1985); Eur. J. Biochem. 143, 277–284 (1984) and Gould I. et al., Eur. J. Biochem. 126, 217–226 (1982).

The oligonucleotides encoding ribozyme are synthesized such that the sequences at the beginning and the end, each consisting of at least 5 nucleotides, preferably 7 to 10 nucleotides are complementary to the RNA of the virus to be inhibited. One part of the sequence lying in 5 between consists of specific nucleotides predetermined for the functionality of the ribozyme and one part consists of variable nucleotides. A diagram of the ribozyme hybridized with substrate RNA can look as in FIG. 1.

The preparation of the antisense RNA is carried out correspondingly but the oligonucleotides are synthesized in such a way that they encode an RNA in the corresponding antisense orientation.

However, the basis for the oligonucleotide synthesis for the ribozyme RNA can also be any substrate desired. In principle, care has only to be taken that the spacer is a substrate for the ribozyme and is provided with the appropriate ribozyme cleavage sites. The spacers for the coupling of the ribozyme and antisense molecules are constructed such that the entire correspondingly expressed RNA, or parts thereof, is complementary to the ribozyme, the complementary nucleotides advantageously grouping around a GUC cleavage site for the ribozyme.

The constructed oligonucleotides are provided with an appropriate linker. Linkers of this type, for example, have cleavage sites of EcoRI, SalI, BamHI, HindIII, EcoRV, SmaI, XhoI, KpnI, preferably XbaI or PstI.

The assembled oligonucleotides are cloned with the aid of the vectors pUC19, pUC18 or pBluescript (Stratagene, Heidelberg, Product Information) and sequenced.

The confirmed oligonucleotide is cloned in an intermediary vector with a plant promoter. Vectors of this type are, for example, the plasmids pPCV701 (Velten J. et al. EMBO J. 3, 2723–2730 (1984)), PNCN (Fromm M. et al. PNAS 82, 5824–5826 (1985)) or PNOS (An G. et al., EMBO J. 4, 277–276 (1985)). The vector pDH51 (Pietrzak, M. et al., NAR 14, 5857, (1986)) with a 35S promoter is preferably used.

After subsequent transformation of *E. coli*, such as for example *E. coli* MC 1061, DH1, DK1, GM48 or XL-1, positive clones are identified by methods known per se (Maniatis et al., Lab. Manual), such as plasmid minipreparation and cleavage with an appropriate restriction enzyme.

These positive clones are then subcloned in a binary plant vector. pGV3850 (Zambrysky, P. et al. EMBO J. 2, 2143–2150 (1983)) or pOCA18 (Olszewski, N., NAR 16, 10765–10782, (1988)) can be employed as plant vectors. pOCA18 is preferably used.

The resulting binary plant vectors which contain a plant promoter with the attached DNA fragment which is constructed as described above in the T-DNA are used to transform plants. This can be carried out by techniques such as electroporation or microinjection.

The cocultivation of protoplasts or the transformation of small pieces of leaves using agrobacteria is preferably employed. For this purpose the plant vector construct is transferred by transformation with purified DNA or, mediated by a helper strain such as *E. coli* SM10 (Simon R. et al., Biotechnology 1, 784–791 (1983)), in Agrobacterium tumefaciens, such as A 282, with a Ti plasmid via a triparental mating. Direct transformation and triparental mating were carried out as described in "Plant Molecular Biology Manual" (Kluwer Academic Publishers, Dardrecht (1988)).

Basically all plants can be transformed with the binary plant vectors carrying the constructed DNA according to the invention. Dicotyledonous plants, in particular useful plants which produce or store, for example, starch, carbohydrates, proteins or fats in usable amounts in their organs or produce fruit and vegetables or provide spices, fibers and technically usable products or pharmaceuticals, dyes or waxes are preferred as are fodder plants.

Tomato, strawberry and avocado as well as plants which carry tropical fruit, for example papaya, mango, but also pear, apple, nectarine, apricot or peach shall be mentioned as examples. Furthermore all types of cereal, rape, potatoes, soybean, cotton, corn, sugarbeet or sunflower shall be listed as examples of plants to be transformed. The transformed cells are selected with the aid of a selection medium, grown to a callus and regenerated to the plant on an appropriate medium (Shain et al, Theor. appl. Genet. 72, 770—770 (1986); Masson, J. et al., Plant Science 53, 167–176 (1987); Zhan et al., Plant Mol. Biol. 11, 551–559 (1988); McGranaham et al., Bio/Technology 6, 800–804 (1988); Novrate et al., Bio/Technology 7, 154–159 (1989)).

The resultant plant is changed by the transformation so far as the RNA expressed with the aid of the constructed oligonucleotides is cleaved on GUC cleavage sites by the ribozyme activity in the cells and antisense RNA is released for this reason, it being possible for ribozyme RNA together with antisense RNA to become active towards virus DNA or RNA.

The examples which follow serve to illustrate the invention further.

EXAMPLES

Percentages relate to weight if not specified otherwise.

1. Synthesis of the DNA for the expression of the multifunctional RNA

The synthesis of the DNA sequence of Table 1 for the expression of the multifunctional RNA was carried out as described below:

a) Ribozyme I [1–46]: the regions homologous to CMV are based on the published RNA 1 sequence (Rezaian M. et al., Eur. J. Biochem. 150, 331–339 (1985)) from position 3248 to 3264. The constant regions for the ribozyme can be seen in Table 1 and were derived from the publication by Haseloff, J. et al., Nature 334, 585–591 (1988).

b) Spacer [47–70]: based on the published RNA 2 sequence (Rezaian, M. et al., Eur. J., Biochem. 143, 277–284 (1984)) from position 2853 to 2870.

c) Antisense 1[71–243]: based on the published RNA 4 sequence (Gould I. et al., Eur. J. Biochem. 143, 217–226 (1982)) from position 2054 to 2193.

d) Spacer [219–243]: as for spacer [47–70] under b.

e) Antisense 2[244–313]: based on the published RNA 2 sequence (see above) from position 71 to 134.

f) Spacer [314–338]: as for spacer [47–70] under b.

g) Antisense 3[339–405]: based on the published RNA 4 sequence (see above) from position 1200 to 1261.

h) Spacer [406–429]: based on the published RNA 1 sequence (see above) from position 3248 to 3264.

i) Ribozyme [430–480]: for the regions homologous to CMV based on the RNA 2 sequence (see above) from position 2853 to 2870; for the constant regions according to Table 1 see publication under a).

The square brackets relate to the positions of the attached DNA sequence for the expression of the multifunctional RNA (Table 1).

With the aid of the phosphoramide method, the oligonucleotides listed in Table 1 were synthesized using a synthesizer. The fragments can be seen from the sequence. The first one extends from the XmaI linker at the start to the KpnI side, the second one from KpnI to BamHI, the third one from BamHI to SacI and the fourth one from SacI to the SmaI junction at the end. Strand and complementary strand were synthesized in each case, which were combined in equimolar amounts before the cloning.

2. Cloning in pBluescript SK+ and sequencing

The plasmid pBluescript SK+ (stratagene, product information) was opened with the particular enzymes (XmaI/KpnI, KpnI/BamHI, BamHI/SacI, SacI/SmaI) and, after treatment with calf intestinal phosphatase (CIP), ligated with a fivefold excess of the double stranded phosphorylated oligonucleotide. After induction by isopropylthiogalactoside (IPTG, Boehringer Mannheim), it was possible to identify positive clones as white colonies in the strain XL- Blue (stratagene) on LB-plates containing 5-bromo- 4-chloro-3-indolyl-β-D-galactoside (X-gal) (Boehringer, Mannheim).

5 of the colonies were isolated in each case and sequenced by the dideoxy termination method (Boehringer, Sequencing Kit). After cleaving with the appropriate enzymes, the oligonucleotide was isolated from a colony with the expected sequence from a highly pure (low melt) agarose gel (Gibco, Brueggenstein, FR Germany).

The isolated oligonucleotides were ligated and separated from nonligated ones on a highly pure (low melt) agarose gel. The expected 0.5 kb band was cut out and, after filling the overhanging XmaI site, inserted into the SmaI recognition sequence of pBluescript SK+.

The photograph in FIG. 2 shows 6 colonies of a plasmid preparation from XL-1 Blue cells which were transformed with the vector pbluescript into which the complete fragment has been incorporated. The plasmids were cut with SmaI before the application onto the gel. In colonies 1–5 a fragment of the expected size can be detected.

3. Cloning of the entire fragment into pDH51

The fragment for the expression of the multifunctional RNA was isolated from the pBluescript construction by digestion with SmaI and was incorporated into an SmaI-cut pDH51. It was possible to determine the orientation of the fragment by HindIII.

The plasmid pDH51 is reproducibly described in Pietrzak, M. et al., NAR 14i, 5857–5869 (1986).

Figure 3:
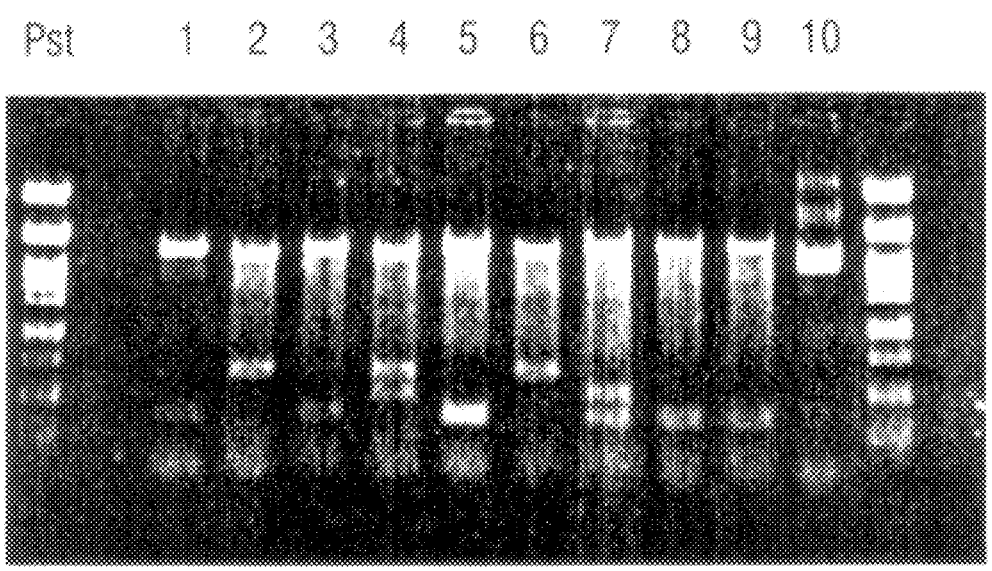
FIG. 3 shows DNA mininpreparations of MC1061 cells after transformation with pDH51 into the multifunctional DNA fragment was incorporated into the SmaI site.

FIG. 3 DNA minipreparations were made of MC1061 cells after transformation with pDH51 into which the multifunctional DNA fragment was incorporated into the SmaI site.

The DNA minipreparations were HindIII-cleaved. An incorporation having the desired orientation appears in 5 of the the preparations.

4. Cloning of the entire fragment with 35S promoter into pOCA18

The 1.2 kb fragment for the expression of the multifunctional RNA was isolated together with the 35S promoter and terminator by an EcoRI-digestion of the pDH51 containing the cloned insert. The isolated fragment was ligated with an EcoRI-cut pOCA18 vector. The vector ligated with the fragment was transferred into MC1061 cells by transformation. The plasmid pOCA18 is reproducibly described in Olszewski, N. et al. NAR 16, 10765–10782 (1988).

Figure 4:
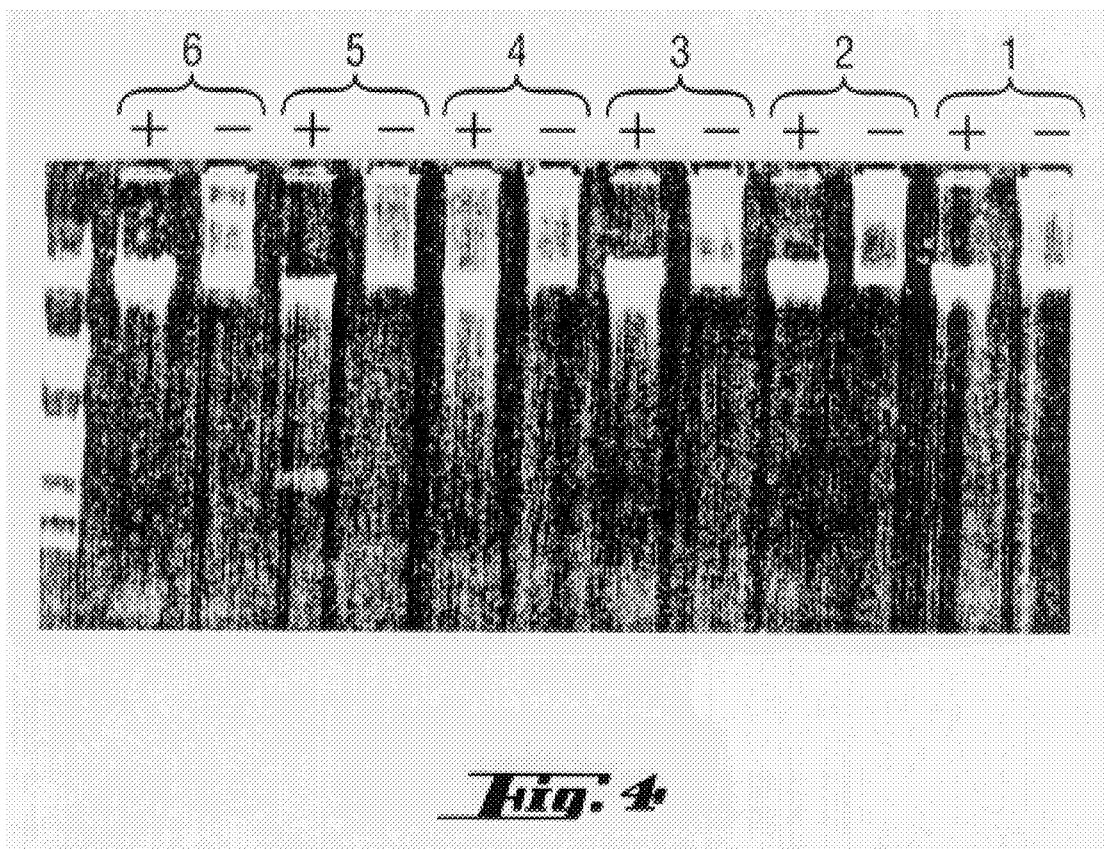
FIG. 4 shows DNA minipreparations from MC1061 cells which were transformed with pOCA18 into which the EcoRI fragment was ligated.

FIG. 4 DNA minipreparations were made from MC1061 cells which were transformed with pOCA18 into which the EcoRI fragment was ligated. The DNA was cleaved with EcoRI (designated "+") before applying it onto the gel. In addition, the same amount of uncleaved DNA was applied in each case ("−"). One colony from this experiment resulted in an EcoRI band of the desired size.

5. Transformation of agrobacteria

The vector pOCA18 containing the 35S promoter/ oligonucleotide insert was transferred into the agrobacteria strain A 282 (Pharmacia, Freiburg, FR Germany, or ATCC 37349, USA). This was effected by a triparental mating with the aid of the E. coli strain SM10 (Simon, R. et al. Bio/ Technology 1, 784–791, 1983). For this purpose equal amounts of the bacteria were placed together on a filter overnight, the filter was rinsed with 2 ml of 10 mM $MgSO_4$ and aliquots thereof were placed on YEB plates containing tetracyclin and rifampicin (YEB: 1% yeast extract, 1% peptone, 0.5% NaCl). It was possible to detect positive agrobacteria by hybridization. For this purpose the colonies are transferred onto "Gene Screen Plus" filters (New England Nuclear, Boston). The filters were incubated at 28° C. on YEB plates overnight, and denatured and neutralized on the next day. Subsequently the filters were hybridized with $4 \times 10^5$ cpm/nl of the radiolabeled entire fragment at 65° C. overnight.

The filters were washed at 65° C. 1 ×with 1 ×SSC and 2 ×with 0.1 ×SSC/SDS for 30 minutes in each case.

Figure 5:
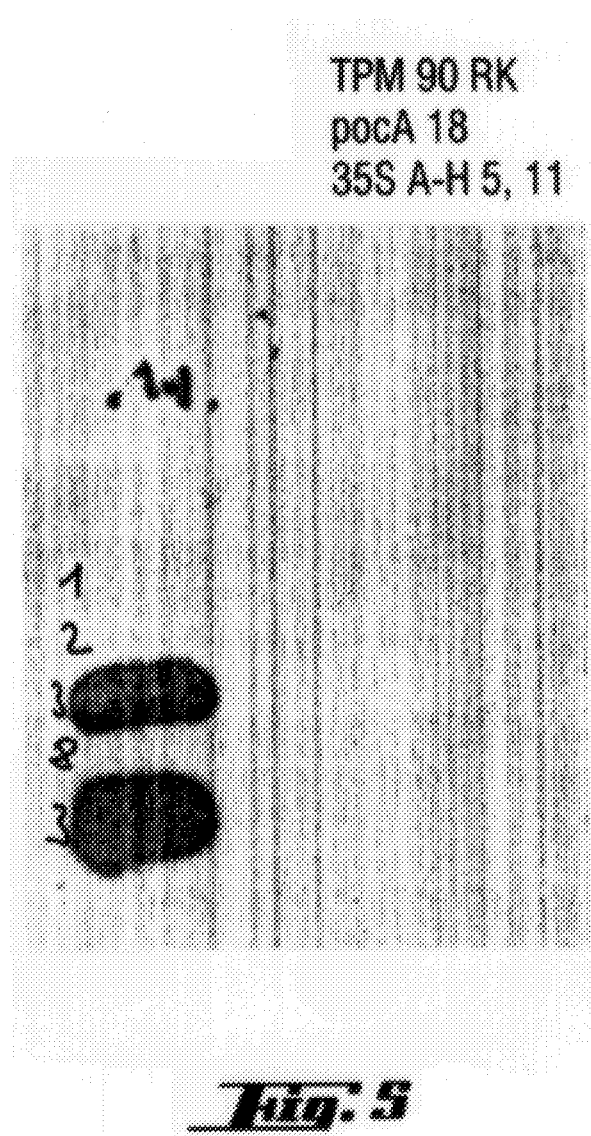
FIG. 5 shows a film which was exposed on the washed filters for 6 hours to confirm the results in Example 5.

FIG. 5 shows film w was exposed on the washed filters for 6 hours. One colony is positive. The latter was applied in duplicate in order to confirm the result of a preceding experiment.

6. Transformation of tobacco

The agrobacteria were grown in YEB medium (1% yeast extract, 1% peptone, 0.5% NaCl) containing tetra- cyclin and rifampicin, 20 ml of the bacteria were centrifuged off, washed once in YEB medium and, suspended in 20 ml of 10 mM $MgSO_4$, placed in a Petri dish. Nicotiana tabacum, Wisconsin 38 was used as plant material. The plants had been cultivated for 4 weeks under sterile conditions on 2MS medium (Murashige T. et al., Physiol. Plant 15, 473–497 (1962)) at 25° C. with 16 h of light per day. A 1 $cm^2$ piece of leaf was cut off from these plants, injured with sterile emery paper and immersed in the bacteria culture for 30 s. The pieces of leaf were maintained on MS medium, as described above for 2MS, at 25° C. for 2 days and then washed using liquid 2MS medium. The pieces of leaf were then placed on MSC 10 (as MS containing 1.5% agar) plates containing kanamycin. After 5–6 weeks it was possible to replant regenerated plants in larger vessels where they formed roots after 2–3 weeks.

DNA was isolated from transgenic tobacco plants by the CTAB method. The protocol of the "Plant Molecular Biology Manual", Kluwer Academic Publishers, Dordrecht (1988) was strictly followed in this connection. 10 µg of the DNA were cleaved with EcoRI, separated on a 1% agarose gel and, after denaturing, transferred onto a "Gene Screen Plus" membrane. The membrane was hybridized with $4 \times 10^5$ cpm/ml of the radiolabeled fragment at 65° C. overnight. It was possible in all cases to detect a fragment of the expected size.

Figure 6:
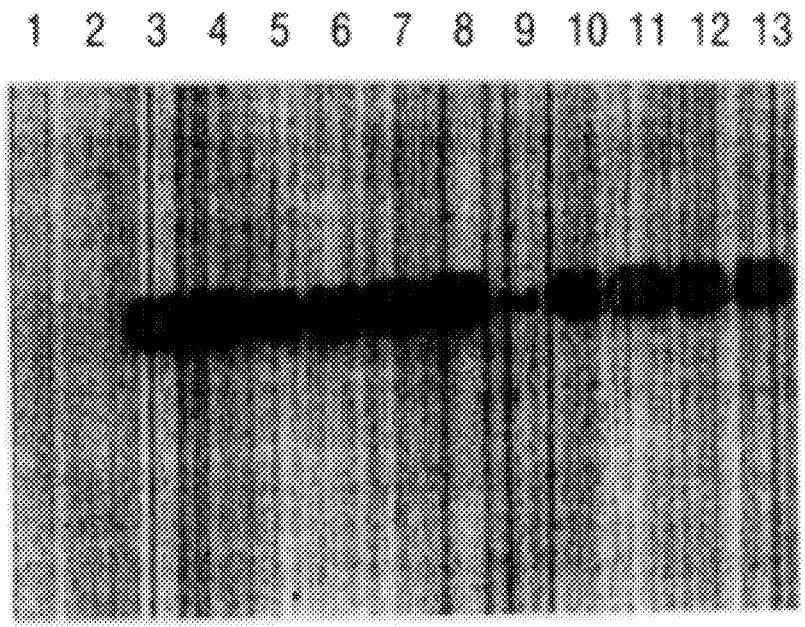
FIG. 6 shows the DNA preparation from transgenic plants discussed in Example 6.

All DNA preparations from transgenic plants show the expected hybridization as a 1.2 kb EcoRI band. (See FIG. 6)

7. Expression of the multifunctional RNA using transgenic tobacco plants

Total RNA was isolated from pieces of leaf of transgenic tobacco plants. The protocol of the "Plant Molecular Biology Manual", Kluwer Academic Publishers, Dordrecht (1988) was followed in this connection. After denaturing, 10 µg of the total RNA were fractionated on a 2.2 M formaldehyde/1% agarose gel in 12 mM tris pH 7.5/0.1 mM EDTA buffer and transferred onto a "Gene Screen Plus" membrane. The membrane was hybridized with radiolabeled entire fragment. The transgenic plants show a strong RNA expression with the expected specificity.

8. Infection of transgenic tobacco plants with CMV

Infection was carried out with the CMV strain Q (Rezaian, M. et al., Eur. J. Biochem. 150, 331 (1985); 143, 277 (1984); Gould, J. et al., Eur. J. Biochem. 126, 217 (1982)) which was obtained from cucumber leaves. The infectious particles were applied to the tobacco plants with the aid of carborundum. Under the selected infection conditions, 80% of the control plants showed severe symptoms which consisted of brightening of the veins, formations of mosaics and irregular growth of the leaf edges. It was possible to confirm specificity of the infection by ELISA.

The test of the transgenicity was carried out on plants which had previously been propagated by cuttings. A confirmation on the progeny was carried out if seeds were present.

It has been found that a strong reduction in the probability of infection had occurred practically in all plants which showed an expression of the multifunctional RNA. Only about 10–50% of the transgenic plants, depending on a specific event of transformation in each case, developed the typical symptoms of infection.

TABLE

Percentages of infected plants having significant symptoms; 10 plants were evaluated in each case

|  |  | 12 days | 20 days |
|---|---|---|---|
| Control Tobacco W38 |  | 80 | 80 |
| Transgenes: | A-H3 | 20 | 30 |
|  | A-H7 | 10 | 20 |
|  | A-H15 | 40 | 50 |
|  | A-H22 | 30 | 30 |

Thus the method used proved to be suitable for protecting plants from viral infections. In order to improve the resistance, it can be attempted to attach even more elements to the multifunctional RNA.

TABLE 1

The top strand of the following DNA sequence that runs in the 5' to 3' direction corresponds to SEQ ID NO:1. The bottom strand of the following DNA sequence that runs in the 3' to 5' direction corresponds to SEQ ID NO:2.

```
XmaI 9            18           27           36
5' CCG GGA GGT AGC TCC TGA TGA GTC CGT GAG GAC GAA ACA ACC
3'     C CCT CCA TCG AGG ACT ACT CAG GCA CTC CTG CTT TGT TGG 54           63           72           81
   TTG TCG TCG ACA AAA TGG TCA GTA TGC CCC TCG AGT GGT CTC
   ACC AGC AGC TGT TTT ACC AGT CAT ACG GGG AGC TCA CCA GAG 90           99          108          117 KpnI    126
   CTT ATG GAG AAC CTG TGG AAA ACC ACA GGC GGT ACC CGC ACT
   GAA TAC CTC TTG GAC ACC TTT TGG TGT CCG CCA TGG GCG TGA 135          144          153          162
   CTT GGT AAT ATC AGT GTA TTA CCG TGC ACG AGC TTC TCA CGA
   GAA CCA TTA TAG TCA CAT AAT GGC ACG TGC TCG AAG AGT GCT 171          180          189          198          207
   AGC CCT TCC GAA GAA ATC TAG GAG ATG ATT TCA AGG GTA GCT
   TCG GGA AGG CTT CTT TAG ATC CTC TAC TAA AGT TCC CAT CGA

216       BamHI 225         234          243         252
   CGA CAA CCT GGA TCC AAA ATG GTC AGT ATG CCC CCC ATG GCA
   GCT GTT GGA CCT AGG TTT TAC CAG TCA TAC GGG GGG TAC CGT 261          270          279          288
   ACA GAT TGG CGA ATG AGA AAG TGG GTG GAG GAC TTA TCA TAG
   TGT CTA ACC GCT TAC TCT TTC ACC CAC CTC CTG AAT AGT ATC 297          306          315          324          333
   TAA CAG AAG AGA GAC TAG AAC TGC AGA AAA TGG TCA GTA TGC
   ATT GTC TTC TCT CTG ATC TTG ACG TCT TTT ACC AGT CAT ACG
```

TABLE 1-continued

The top strand of the following DNA sequence that runs in the 5' to 3' direction corresponds to SEQ ID NO:1. The bottom strand of the following DNA sequence that runs in the 3' to 5' direction corresponds to SEQ ID NO:2.

```
       342         351         360         369     SacI  378
CCC AGA TCT ACC GGA GGT TCT ACT AGC ATT GGG AGA GCT CGA
GGG TCT ACA TGG CCT CCA AGA TGA TCG TAA CCC TCT CGA GTC 387         396         405         414
TTT GTC CAT AGG CAC ACT GAG ACG CAA AAA GCT TAA GGT TGT
AAA CAG GTA TCC GTG TGA CTC TGC GTT TTT CGA ATT CCA ACA 423         432         441         450         459
CGA GCT ACC GGG GCC CAG GGC ATA CTC TGA TGA GTC CGT GAG
GCT CGA TGG CCC CGG GTC CCG TAT GAG ACT ACT CAG GCA CTC 468         477  Sma
GAC GAA ACC ATT TTG GG 3'
CTG CTT TGG TAA AAC CC 5'
```

We claim:

1. Plants, plant cells and parts or seeds of the plants, which contain a gene coding for a ribozyme RNA sequence coupled to an antisense RNA sequence by a spacer wherein the spacer contains a cleavage site cleaved by said ribozyme.

2. Plants, plant cells and parts or seeds of the plants, which contain a multifunctional RNA encoded by the gene as recited in claim 1.

3. A method of inhibiting a virus in a plant cell comprising inserting an antiviral effective amount of the gene of claim 1 into said plant cell, wherein the antisense RNA encoded by said gene of claim 1 is complementary to the viral RNA of said virus, wherein said virus is inhibited.

4. A method of inhibiting a virus in a plant cell comprising inserting an antiviral effective amount of the gene of claim 1 into said plant cell, wherein the ribozyme RNA encoded by said gene of claim 1 is complementary to the viral RNA of said virus, wherein said virus is inhibited.

5. Plants, plant cells and parts or seeds of the plants, which contain an isolated DNA fragment which encodes a pattern which comprises:

5'-hammerhead ribozyme RNA-spacer-antisense RNA-(spacer-antisense RNA)$_n$-spacer-hammerhead ribozyme RNA-3', wherein n is a number from 0 to 9, and the spacer is a chain of 20 to 25 nucleotides which contains a ribozyme cleavage site in each case; and wherein said DNA fragment encodes a multifunctional RNA with self-processing activity.

6. Plants, plant cells and parts or seeds of the plants, which contain a multifunctional RNA with self-processing activity.

7. A method of inhabiting a virus in a plant cell comprising inserting an antiviral effective amount of the isolated DNA fragment of claim 5 into said plant cell, wherein the antisense RNA encoded by said isolated DNA fragment of claim 5 is complementary to the viral RNA of said virus, wherein said virus is inhibited.

8. A method of inhabiting a virus in a plant cell comprising inserting an antiviral effective amount of the isolated DNA fragment of claim 5 into said plant cell, wherein the ribozyme RNA encoded by said isolated DNA fragment of claim 5 is complementary to the viral RNA of said virus, wherein said virus is inhibited.

* * * * *

UNITED STATES PATENT AND TRADEMARK OFFICE
CERTIFICATE OF CORRECTION

PATENT NO. : 5,834,265
DATED : November 10, 1998
INVENTOR(S) : Hubert Müllner et al.

It is certified that error appears in the above-identified patent and that said Letters Patent is hereby corrected as shown below:

Title page,
Item [75], line 3, after "both of Kelkheim", insert -- all of Germany --;
Lines 4-5, "All of Germany" should read -- The Netherlands --.

Column 12, claim 6,
Line 42, "with self-processing activity" should read -- encoded by the isolated DNA fragment as recited in Claim 5 --.

Column 12, claim 7,
Line 43, "inhabiting" should read -- inhibiting --.

Column 12, claim 8,
Line 50, "inhabiting" should read -- inhibiting --.

Signed and Sealed this

Sixteenth Day of April, 2002

Attest:

Attesting Officer

JAMES E. ROGAN
Director of the United States Patent and Trademark Office